United States Patent [19]

Shimoda

[11] Patent Number: 5,188,629
[45] Date of Patent: Feb. 23, 1993

[54] CLOSING APPLIANCE USED IN FLEXIBLE TUBE

[75] Inventor: Keitaro Shimoda, Kusatsu, Japan
[73] Assignee: Nissho Corporation, Osaka, Japan
[21] Appl. No.: 717,593
[22] Filed: Jun. 19, 1991
[30] Foreign Application Priority Data
 Jun. 21, 1990 [JP] Japan ............................ 2-65600[U]
[51] Int. Cl.⁵ .............................................. A61M 5/14
[52] U.S. Cl. ..................................... 604/412; 604/403; 604/408; 604/905
[58] Field of Search .................... 604/408, 410–416, 604/905

[56] References Cited
U.S. PATENT DOCUMENTS 3,217,710 11/1965 Beall et al. ........................ 604/408
4,007,738 2/1977 Yoshino ............................ 604/410
4,181,140 1/1980 Bayham et al. ................. 604/249 X
4,340,049 7/1982 Munsch ........................... 604/905 X Primary Examiner—Robert A. Hafer
Assistant Examiner—Sam Rimell
Attorney, Agent, or Firm—Nikaido, Marmelstein, Murray & Oram

[57] ABSTRACT

A closing appliance used in a flexible tube comprising a communicating tube, a column-like portion, and a thin-walled portion formed between the communicating tube and column-like portion. The column-like portion has two wings facing to each other at an end opposite to the thin-walled portion. The wings have rounded surface on the side of the inner surface of the flexible tube, and a total lateral sectional area of the two wings is from 25 to 50% of a sectional area of a hollow portion of the flexible tube. Thanks to wings, damage of the flexible tube on centrifugal separation process can be avoided.

1 Claim, 3 Drawing Sheets

CLOSING APPLIANCE USED IN FLEXIBLE TUBE

BACKGROUND OF THE INVENTION

The present invention relates to a closing appliance used in a flexible tube which connects blood bags without damaging sterility in the system.

When blood is collected from a donor, cellular components of blood are usually separated from plasma prior to storage or use thereof. In general, separation of blood is carried out by centrifugal separation method whereby blood is separated into an upper plasma layer, a middle thin soft-film-like layer probably containing platelets and white cells, and a lower layer comprising red cells.

Bags made of synthetic resin are used in separating blood into cellular components and plasma. FIG. 4 is a plan view of an example of a double-type blood bag, and FIG. 5 is a sectional view explaining a conventional closing appliance in a flexible tube. Blood is collected into a blood bag 11 through a blood-collecting-tube 15. After collection is performed, the blood-collecting-tube 15 is sealed near the blood bag 11 and a part of the blood-collecting-tube 15 including a blood-collecting-needle (not shown) is separated from the residual portion. Then, both the blood bag 11, and a child bag 12 connected to the blood bag 11 through a connector 13 and a connecting tube 14 are processed by centrifugal separation method.

After centrifugal separation, plasma separated from blood is moved into the child bag 12 through a communicating tube 2 of the closing appliance and the connecting tube 14, by holding the connector 13 with hands and breaking a thin-walled portion 4 of the closing appliance.

On carrying out centrifugal separation in the above-mentioned process, however, there is a problem of the flexible tube that a tip 7 of the closing appliance frequently break through.

It is an object of the present invention to provide a closing appliance having an improved tip which does not break through a flexible tube.

SUMMARY OF THE INVENTION

In accordance with the present invention, there is provided a closing appliance used in a flexible tube for passing fluid comprising:

(a) a communicating tube having an outer diameter a little larger than an inner diameter of the flexible tube, (b) a column-like portion formed integrally with the communicating tube and having an outer diameter smaller than that of the communicating tube.

(c) a thin-walled portion formed between the column-like portion and the communicating tube, and having a thickness less than that of the communicating tube wherein the column-like portion has two wings at an end opposite to the thin-walled portion, the wings face to each other and have rounded surface on the side of an inner surface of the flexible tube, the rounded surface corresponds to the inner surface of the flexible tube, and a total lateral sectional area of the two wings is from 25 to 50% of a sectional area of a hollow portion of the flexible tube.

A closing appliance of the present invention has two wings each having a rounded surface which corresponds to the inner surface of a flexible tube in which the closing appliance is placed. Accordingly, the force applied to the inner surface of the flexible tube by the wings is reduced, so that the breakage of the flexible tube is avoided.

DETAILED DESCRIPTION

Now, a closing appliance of the present invention is explained in detail based on the accompanying drawings.

Figure 1:
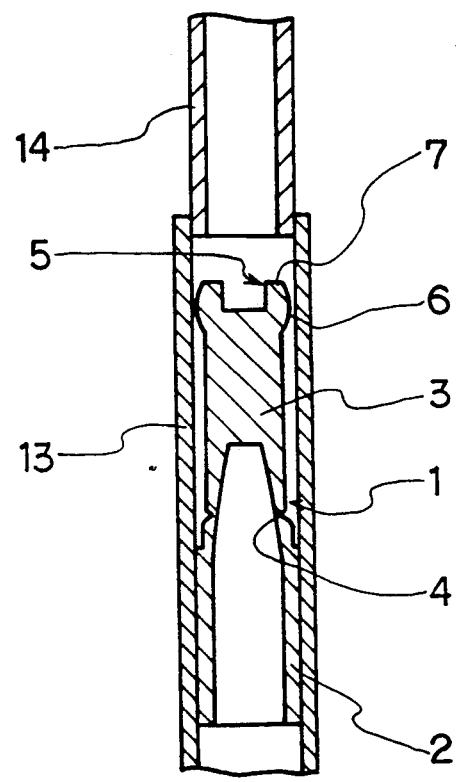
FIG. 1 is an explanatory sectional view of an embodiment of a closing appliance of the present invention in a flexible tube.

FIG. 1 is an explanatory sectional view of an embodiment of a closing appliance of the present invention in a flexible tube.

In FIG. 1, numeral 1 is a closing appliance comprising a communicating tube 2 and a column-like portion 3.

The closing appliance 1 is made of rigid material such as hard synthetic resin. Concrete examples of available synthetic resin are, for example, polycarbonate, polyvinyl chloride, polystyrene and polyethylene terephthalate.

The size of the communicating tube 2 is determined in consideration of the size of a flexible tube. That is, the outer diameter of the communicating tube 2 is so determined as to be a little larger than the inner diameter of the flexible tube. In general, the outer diameter, inner diameter and length of a typical example of the communicating tube are about 5 mm, about 4 mm and 10 to 12 mm, respectively.

At one end of the communicating tube 2, the column-like portion 3 is integrally formed with the communicating tube 2. The column-like portion 3 has an outer diameter smaller than that of the communicating tube 2. The length of the column-like portion 3 is, for example, from 10 to 12 mm.

Between the column-like portion 3 and the communicating tube 2, there is formed a thin-walled portion 4 having a thickness less than that of the communicating tube 2. The thin-walled portion 4 serves to fascilitate the breakage of the closing appliance 1 after centrifugal separation process.

Figure 2:
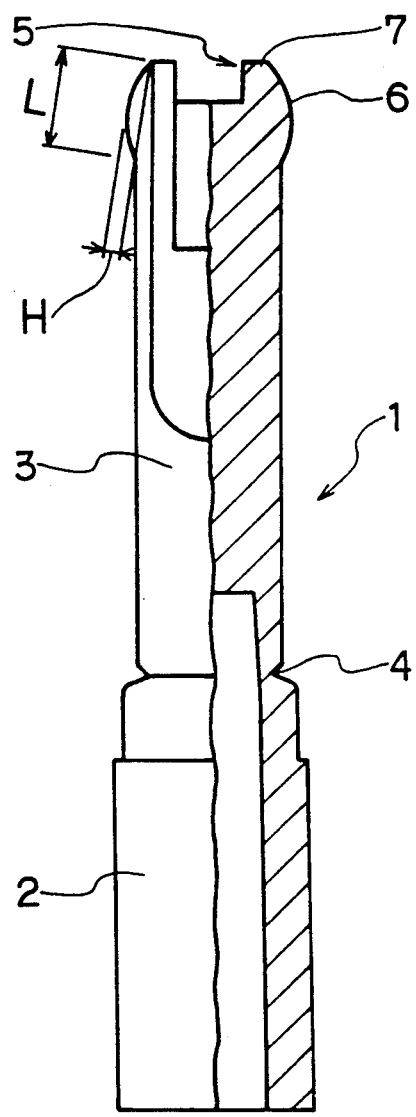
FIG. 2 is an enlarged front view, partially including sectional view, of the closing appliance in FIG. 1.
Figure 3:
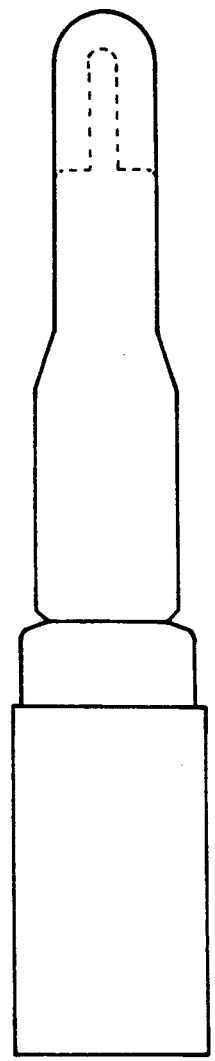
FIG. 3 is an enlarged side view of the closing appliance in FIG. 1.
Figure 4:
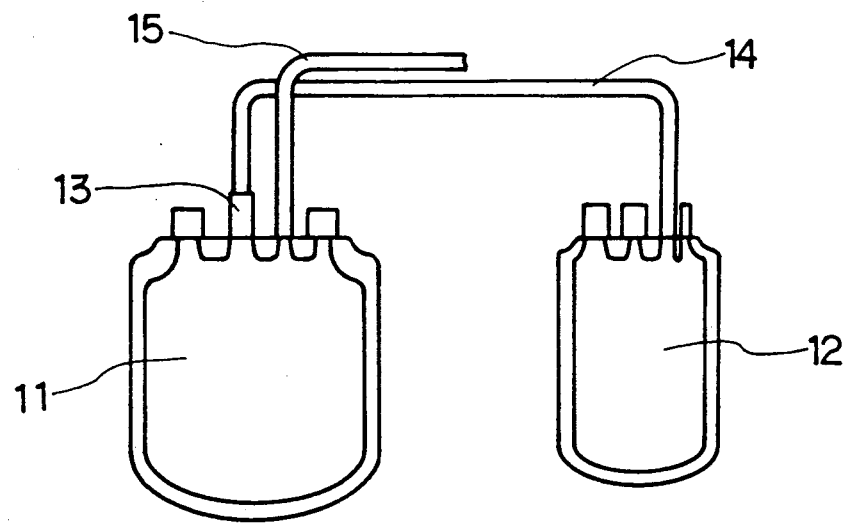
FIG. 4 is a plan view of an example of a double-type blood bag.
Figure 5:
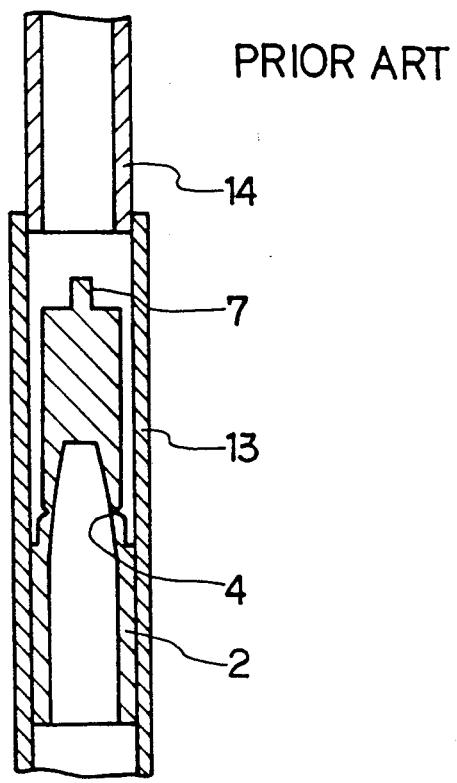
FIG. 5 is a sectional view explaining a conventional closing appliance in a flexible tube.

In the closing appliance of the present invention, the column-like portion 3 has two wings 5 at an end opposite to the thin-walled portion 4. The wings 5 face to each other as shown in FIG. 2, and have rounded surface 6 on the side of the inner surface of the flexible tube. Each rounded surface 6 is so designed as to correspond to the inner surface of the flexible tube in order to reduce the force applied to the inner surface of the flexible tube by the wings 5 on centrifugal separation process.

In the closing appliance of the present invention, it is necessary to determine the total lateral sectional area of two wings 5 not more than 50% of the hollow sectional area of the flexible tube in order to smoothly moving plasma separated from blood into a child bag 12 through the communicating tube 2 and connecting tube 14. On the other hand, the lower limit is required to be 25%. When the above-mentioned total sectional area is less than 25% of the hollow sectional area of the flexible tube, a tip 7 of the wing becomes so sharp that the tip 7 damages the flexible tube on centrifugal separation process.

After centrifugal separation, the connector 13 is held with hands and the thin-walled portion 4 of the closing appliance 1 is broken. Then, plasma separated from blood is moved into the child bag 12 through the communicating tube 2, gap between the column-like portion 3 and the flexible tube, the nearest wings 5 and connecting tube 14.

EXAMPLE

A closing appliance was made by integral molding of polypropylene resin. A communicating tube had an outer diameter of 4.8 mm, inner diameter of 4.25 mm, and a length of 10.5 mm. A column-like portion had an outer diameter of 3.58 mm, and a length of 10.0 mm.

Two wings facing to each other were provided at one end of the closing appliance. Each wing had a length of a chord of 1.35 mm (refer to L in FIG. 2), and a length of circular arc was 2.55 mm while a height of circular arc (refer to H in FIG. 2) was 1.20 mm.

Using the above-mentioned closing appliance, blood collection and blood separation were carried out. No damage was observed in the connecting tube made of polypropylene.

It took 89 seconds (average value of five experiments) to move plasma from a blood-collecting bag (content: 400 ml) to a child bag.

COMPARATIVE EXAMPLE 1

The same procedure as in example was repeated except that the number of wing was one and polyvinyl chloride was used as material for connecting tubes. Damage was observed in 44% of connecting tubes made of polyvinyl chloride.

The time required for moving plasma was 88 seconds (average value of five experiments).

COMPARATIVE EXAMPLE 2

The same procedure as in example was repeated except that the number of wings was four and polyvinyl chloride was used as material for connecting tubes. No damage was observed in the connecting tube made of polyvinyl chloride.

The time required for moving plasma was as much as 127 seconds (average value of five experiments).

According to the closing appliance of the present invention, a tip of the closing appliance does not break through a flexible tube, and separation of blood can be carried out rapidly, because the shape of the closing appliance is improved.

What is claimed is:

1. A closing appliance used in a flexible tube for passing fluid, comprising:
   (a) a communicating tube having an outer diameter slightly larger than an inner diameter of the flexible tube,
   (b) a column-like portion formed integrally with the communicating tube and having an outer diameter smaller than that of the communicating tube,
   (c) a thin-walled portion formed between the column-like portion and the communicating tube, and having a thickness less than that of the communicating tube wherein the column-like portion has two wings at an end opposite to the thin-walled portion, the wings face to each other and have an arcuately rounded surface on the side of an inner surface of the flexible tube, wherein a curvature of the rounded surface corresponds to a portion of the inner surface of the flexible tube, a maximum diameter of the column-like portion including the wings is smaller than the inner diameter of the communicating tube, and a total lateral sectional area of the two wings is from 25 to 50% of a sectional area of a hollow portion of the flexible tube.

* * * * *